(12) United States Patent
Giersch et al.

(10) Patent No.: US 9,345,489 B2
(45) Date of Patent: May 24, 2016

(54) REAMING DEVICE WITH CARBON FIBER SHAFT AND MOLDED INTERFACE ELEMENT

(71) Applicant: Stryker Trauma GmbH, Schönkirchen (DE)

(72) Inventors: Helge Giersch, Laboe (DE); Ingo Stoltenberg, Probsteierhagen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 74 days.

(21) Appl. No.: 14/175,346

(22) Filed: Feb. 7, 2014

(65) Prior Publication Data
US 2014/0155900 A1    Jun. 5, 2014

Related U.S. Application Data

(63) Continuation of application No. 13/075,611, filed on Mar. 30, 2011, now abandoned.

(30) Foreign Application Priority Data

Mar. 31, 2010 (EP) ...................................... 10158573

(51) Int. Cl.
*A61B 17/16* (2006.01)
*B29C 45/14* (2006.01)
(Continued)

(52) U.S. Cl.
CPC ............. *A61B 17/162* (2013.01); *A61B 17/164* (2013.01); *B29C 45/14786* (2013.01); *A61B 2017/00526* (2013.01); *A61B 2019/307* (2013.01)

(58) Field of Classification Search
CPC ............... A61B 17/16; A61B 17/1615; A61B 17/1617; A61B 17/162; A61B 17/164; A61B 2017/00526; A61B 2019/307; B29C 45/14786

USPC .......... 606/79, 80, 86 R–89, 96–98; 173/176; 403/2, 27–30; 408/226; 81/468, 471; 411/8, 13, 14
See application file for complete search history.

(56) References Cited

U.S. PATENT DOCUMENTS

| 119,232 | A | 9/1871 | Jones |
| 752,669 | A | 2/1904 | Wuzowski |

(Continued)

FOREIGN PATENT DOCUMENTS

| CH | 668690 A5 | 1/1989 |
| EP | 253526 A1 | 1/1988 |

(Continued)

OTHER PUBLICATIONS

International Search Report and Written Opinion, PCT/EP2007/006771, dated May 8, 2008.

(Continued)

*Primary Examiner* — Christian Sevilla
*Assistant Examiner* — Eric S Gibson
(74) *Attorney, Agent, or Firm* — Lerner, David, Littenberg, Krumholz & Mentlik, LLP

(57) ABSTRACT

A reaming device comprising a shaft with a mounting portion, the mounting portion having an outer surface; a carbon fiber layer located on the mounting portion outer surface; an injection molded interface element for mechanical coupling of an external device molded on the carbon fiber layer, the interface element having a mounting portion; wherein the carbon fiber layer extends over the outer surface of the shaft mounting portion and having an outer surface, wherein the carbon fiber layer outer surface has a non-smooth surface structure; wherein the injection molded interface element mounting portion is injection molded over the carbon fiber layer surface structure The method according to claim 12, further comprising preparing of shaft mounting portion before wrapping a carbon fiber layer for establishing a reliable connection between the shaft and the carbon fiber layer.

17 Claims, 2 Drawing Sheets

(51) Int. Cl.
*A61B 17/00* (2006.01)
*A61B 19/00* (2006.01)

(56) References Cited

U.S. PATENT DOCUMENTS

| | | | |
|---|---|---|---|
| 1,317,624 A | 9/1919 | Herrman | |
| 3,706,154 A | 12/1972 | Luebbers et al. | |
| 3,751,176 A | 8/1973 | Von Hollen | |
| 4,113,480 A | 9/1978 | Rivers | |
| 4,149,391 A | 4/1979 | Driver | |
| 4,185,472 A | 1/1980 | Yates et al. | |
| 4,362,521 A | 12/1982 | Puck et al. | |
| 4,401,396 A | 8/1983 | McKay | |
| 4,605,385 A | 8/1986 | Puck et al. | |
| 4,624,486 A | 11/1986 | Nishino et al. | |
| 4,647,078 A | 3/1987 | Lundy | |
| 4,654,795 A | 3/1987 | Shimoni | |
| 4,664,644 A | 5/1987 | Kumata et al. | |
| 4,706,659 A | 11/1987 | Matthews et al. | |
| 4,751,922 A | 6/1988 | DiPietropolo | |
| 4,752,165 A * | 6/1988 | Wanner | 408/239 R |
| 4,792,320 A | 12/1988 | Nickel | |
| 4,900,049 A | 2/1990 | Tseng | |
| 4,932,924 A | 6/1990 | Lobel | |
| 5,028,367 A | 7/1991 | Wei et al. | |
| 5,122,134 A | 6/1992 | Borzone et al. | |
| 5,152,642 A * | 10/1992 | Pitts et al. | 408/226 |
| 5,203,595 A | 4/1993 | Borzone et al. | |
| 5,288,109 A | 2/1994 | Auberon et al. | |
| 5,342,464 A | 8/1994 | McIntire et al. | |
| 5,488,761 A | 2/1996 | Leone | |
| 5,601,493 A | 2/1997 | Nakazono et al. | |
| 5,632,685 A | 5/1997 | Myers | |
| 5,697,929 A | 12/1997 | Mellinger | |
| 5,746,957 A | 5/1998 | Fanelli et al. | |
| 6,053,922 A | 4/2000 | Krause et al. | |
| 6,260,451 B1 | 7/2001 | Mirabito | |
| 6,336,986 B1 * | 1/2002 | Lee et al. | 156/172 |
| 6,350,204 B1 | 2/2002 | Yasui et al. | |
| 6,416,517 B2 | 7/2002 | Harder et al. | |
| 6,419,490 B1 | 7/2002 | Kitchings Weathers, Jr. | |
| 6,656,195 B2 | 12/2003 | Peters et al. | |
| 6,692,365 B2 | 2/2004 | Suzuki et al. | |
| 7,131,982 B1 | 11/2006 | Karapetyan | |
| 7,632,275 B2 * | 12/2009 | Williams et al. | 606/80 |
| 2004/0133208 A1 | 7/2004 | Weikel et al. | |
| 2005/0043739 A1 | 2/2005 | Sullivan et al. | |
| 2005/0115368 A1 | 6/2005 | Prager et al. | |
| 2006/0058105 A1 | 3/2006 | Evans et al. | |
| 2006/0085004 A1 | 4/2006 | Chien | |
| 2007/0015107 A1 | 1/2007 | Mannschedel et al. | |
| 2008/0312654 A1 * | 12/2008 | Weatherdon et al. | 606/53 |
| 2009/0143524 A1 | 6/2009 | Nakayama et al. | |
| 2010/0029818 A1 | 2/2010 | Schachtely et al. | |
| 2010/0113169 A1 | 5/2010 | Ryu | |
| 2010/0152386 A1 | 6/2010 | Miwa et al. | |
| 2010/0239380 A1 | 9/2010 | Amirov et al. | |
| 2010/0286698 A1 | 11/2010 | Del Rio et al. | |
| 2011/0245831 A1 | 10/2011 | Giersch et al. | |
| 2011/0245832 A1 | 10/2011 | Giersch et al. | |

FOREIGN PATENT DOCUMENTS

| | | |
|---|---|---|
| EP | 1832240 A2 | 9/2007 |
| JP | 61-274833 A | 12/1986 |
| WO | 89/08429 A1 | 9/1989 |
| WO | 2006046789 A1 | 5/2006 |
| WO | 2009/015672 A1 | 2/2009 |
| WO | WO 2009/015672 * | 2/2009 |

OTHER PUBLICATIONS

SGL Carbon Group, SIGRATEX, Textile Products Made from Carbon Fibers, 2004.
European Search Report, EP 10158573, dated Oct. 21, 2010.
European Search Report, EP 10158572, dated Oct. 21, 2010.
"Mechanical Interlocking" Encyclopaedia Britannica Online, Encyclopaedia Britannica Inc., 2011. http://www.britannica.com/EBchecked/topic/371863/mechanical-interlocking.
"Carbon-fibre-reinforced polymer" Wikipedia. Retrieved from the Internet on Oct. 14, 2011. URL: http://en.wikipedia.org/wiki/Carbon_fibre-reinforced_polymer.
.Materials Data Book. Cambridge University Engineering Department, n.d. Web Feb. 27, 2013. <http://www-mdp.eng.cam.ac.uk/web/library/enginfo/cueddatabooks/materials.pdf>.

* cited by examiner

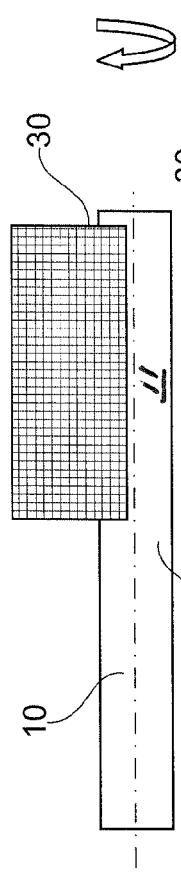
Fig. 1
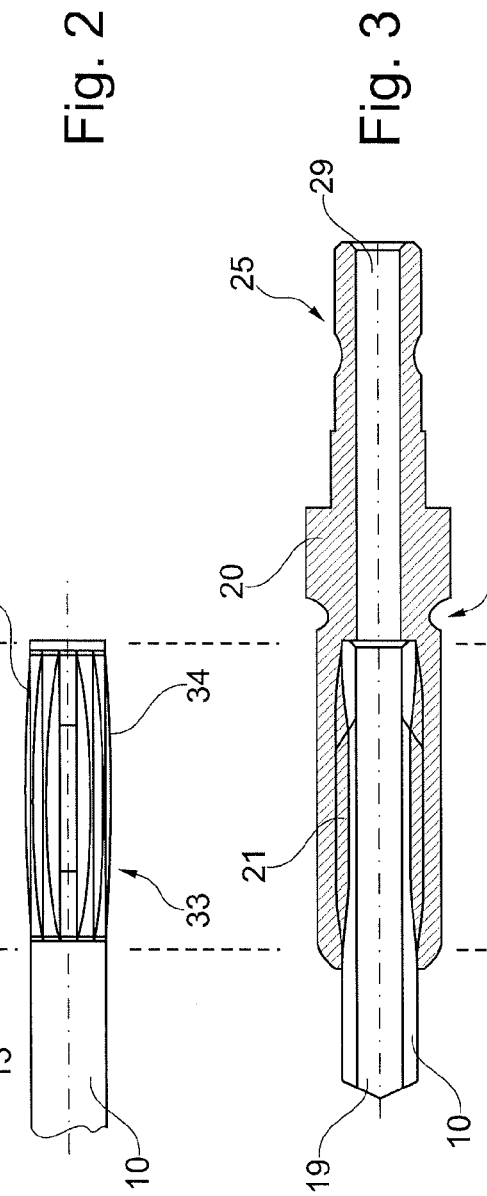
Fig. 2
Fig. 3
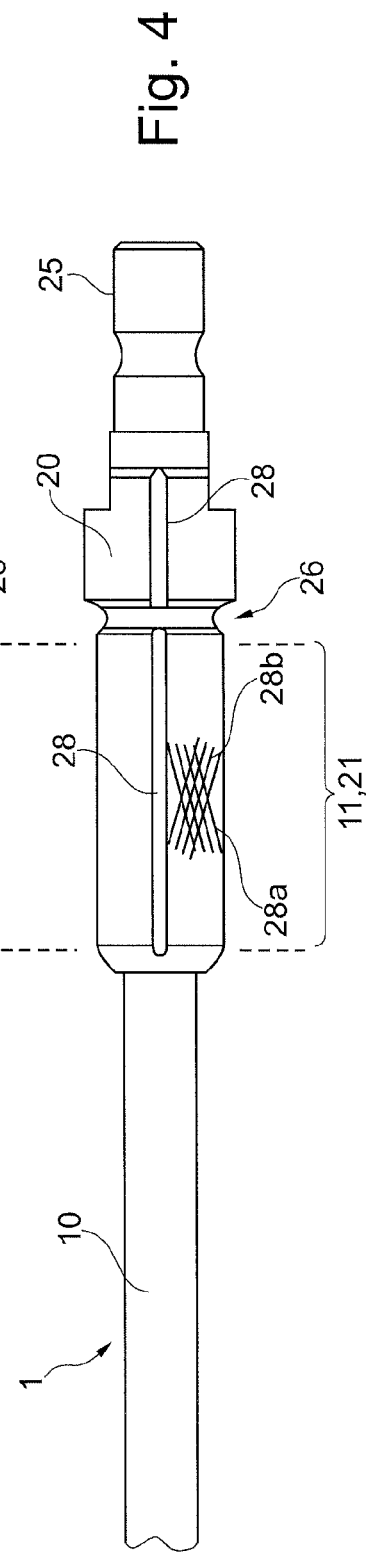
Fig. 4

REAMING DEVICE WITH CARBON FIBER SHAFT AND MOLDED INTERFACE ELEMENT

CROSS REFERENCE TO RELATED APPLICATION

This application is a continuation of U.S. application Ser. No. 13/075,611 filed Mar. 30, 2011, which claims priority from European Patent Application No. 10158573.5 filed Mar. 31, 2010, which is incorporated herein by reference.

BACKGROUND OF THE INVENTION

The present invention relates to a reaming device, and in particular to a reaming device providing a reliable connection between a carbon fiber composite shaft and an interface element molded thereon.

Intramedullary nailing is the method of choice for the fixation of fractures in long bones, in particular bones in long extremities. To have full access to the intramedullary channel, a shaft of a reamer has to be flexible enough in a bending direction to bypass soft tissue and conform to bone curvature. The shaft also has to be rigid enough to convey torsion to the reamer head. Prior art reaming devices have a shaft design consisting of a helix in which residues can be trapped during the reaming procedure, so that the cleaning of the reaming device in hospitals prior to the next usage is complicated, in particular in a sterilization process. The adequate cleaning of the instrument in hospitals demands a great effort and takes a lot of time. Further, some hospitals are not prepared to clean such critical devices because of the great effort involved.

In some prior art reaming devices, a helix shaft is replaced by a shaft made of so called nitinol, which is a material having a high degree of elasticity (super elasticity) to provide enough flexibility. Nitinol is an acronym for NIckel TItanium Naval Ordnance Laboratory. Nitinol is the inter-metallic phase NiTi having a regular cubic crystal structure being different of the structure of titanium or nickel. Nitinol comprises about 55% nickel and about 45% titanium. Owing to the fact that the nitinol shaft is made of a single tube, the cleaning effort in the hospital is less exhausting. However, recent investigations have shown that the nitinol material has a catastrophic failure mode. In particular, some reports have pointed out that some breakages in multiple fragments of the nitinol shaft occurred during the reaming process during the intervention process in hospitals. Further, the nitinol material is a very expensive material.

EP 253526 and U.S. Pat. No. 4,751,922 relates to a shaft made of a composite material of filamentous fibers and an appropriate resin.

From US 2007/0015107, a root canal instrument having an abrasive coating and method for the production thereof is known, wherein the described root canal instrument has a core of a flexible elastic material having a shape memory, wherein the core furthermore has a coating with abrasive particles, wherein the core is made from a nickel-titanium alloy or from a plastic material, e.g. carbon fibre reinforced plastics material.

CH 668690 relates to a probe electrode cable for medical purposes, e.g. electro cardiogram test, using carbon fibre impregnated plastic insulating coating as a cover with a lead coupled to the test equipment.

US Patent Publication No. 2010/0239380 relates to a reaming device with a carbon fiber shaft, an interface element and a connecting agent. The disclosure of 2010/0239380 is incorporated herein by reference.

BRIEF SUMMARY OF THE INVENTION

It is one aspect of the present invention to provide a more reliable reaming device.

One aspect of the present invention is solved by a reaming device comprising a shaft with a mounting portion, the mounting portion having an outer surface. A carbon fiber layer located on the mounting portion outer surface. An injection molded interface element for mechanical coupling of an external device molded on the carbon fiber layer, the interface element having a mounting portion. The carbon fiber layer extends over the outer surface of the shaft mounting portion and has an outer surface. The carbon fiber layer outer surface has a non-smooth surface structure. The injection molded interface element mounting portion is injection molded over the carbon fiber layer surface structure. The shaft of the reaming device is made of a carbon fiber reinforced material. The carbon fiber layer comprises a wrapped carbon fiber with a resin impregnation. The carbon fiber layer surface structure comprises a pressed tooth structure. The pressed tooth structure comprises an elongated rippled structure. The interface element comprises a coupling portion for coupling a power tool reamer drive as an external device. The coupling portion comprises an end portion being capable of transmitting a torque. The injection molded interface element comprises a rated break section between its mounting portion and its coupling portion. The injection molded interface element comprises a mold material having shape stability at common sterilization temperatures, wherein the injection molded interface element comprises a deformation indicating pattern indicating a pre-breaking deformation. Both, the shaft and the interface element each have an elongated through bore, the both through bores aligning to each other.

A method for manufacturing a reaming device, comprises wrapping a carbon fiber layer over an outer surface of a mounting portion of a shaft. A surface structure is pressed on an outer surface of the carbon fiber layer. An interface element is injection molded over the surface structure. The wrapping comprises impregnating the carbon fiber layer with an impregnation agent being compatible with a material of the shaft. The shaft mounting portion is prepared before wrapping a carbon fiber layer for establishing a reliable connection between the shaft and the carbon fiber layer. The pressing includes heat setting of the carbon fiber layer in a closed mold. According to an exemplary embodiment of the invention, a reaming device has a shaft with a mounting portion. The mounting portion has an outer surface, a carbon fiber layer and an injected-molded interface element for mechanically coupling an external device. The injected-molded interface element has a mounting portion. The carbon fiber layer extends over the outer surface of the shaft mounting portion and has its own surface. The carbon fiber layer outer surface has a surface structure. The injection-molded interface element mounting portion is injection-molded over the carbon fiber layer outer surface structure. Thus, the shaft can be provided with an outer surface structure, so that an injection-molded interface element can be easily integrally formed on the shaft, i.e. the carbon fiber layer extending over the shaft. Thus, the shaft can be designed to fulfill the particular requirements for a shaft, for example flexibility and a particular strength against breakage and wherein the integrally formed injection-molded interface element may be designed to fulfill the particular requirements for coupling an external device. Such requirements may include for example a particular geometry and particular material properties which may be met by the injection-molded interface element.

According to an exemplary embodiment of the invention, the shaft is made of a carbon fiber reinforced material. Thus, a particular strength for preventing a breakage of a shaft can be provided, in particular as a carbon fiber reinforced material has a particular flexibility and elasticity while maintaining the capability of transmitting torque forces, and at the same time owing to the carbon fiber reinforced structure does not tend to break into multiple fragments.

According to an exemplary embodiment of the invention, the carbon fiber layer comprises a wrapped carbon fiber with a resin impregnation. Thus, it is possible to bring the carbon fiber layer into a particular shape which is required for molding over the interface element. In particular, the resin impregnation may be a thermosetting resin, so that a particular cast can be heated to set the resin impregnation of the carbon fiber layer.

According to an exemplary embodiment of the invention, the carbon fiber layer surface structure comprises a pressed tooth structure. Thus, a reliable connection between the shaft and the carbon fiber layer, respectively, on the one hand and the molded interface element on the other hand may be established. In particular, a tooth structure allows for a mechanically reliable force transmission between the shaft and the interface element.

According to an exemplary embodiment of the invention, the interface element comprises a coupling portion for coupling a power tool reamer drive as an external device. Thus, a drive or any other power tool may be coupled to the coupling portion of the interface element in order to drive the shaft.

According to an exemplary embodiment of the invention, the coupling portion comprises an end portion being capable of transmitting a torque. Thus, a torque of a power tool can be transmitted to the shaft via the interface element. In particular, the end portion may be designed as a hexagonal cross-section. However, it should be noted that also any other angular geometry may be used. It should be noted that also a free-shape cross-section may be used, e.g. having a waved outer contour. In particular, a unique cross-sectional shape may be used in order to guarantee the correct use of a particular tool together with the corresponding reaming device. In other words, the coupling of an intended combination of a reaming device and a corresponding power tool may be established by a unique corresponding coupling geometry between the power tool and the respective coupling portion or end portion of the interface element.

According to an exemplary embodiment of the invention, the injection-molded interface element comprises a rated break arrangement or geometry (having a predetermined sheer strength) between its mounting portion and its coupling portion. Thus, a predetermined breaking point or a weak section can be established so that the reaming device will break at this particular section when exceeding a predetermined torque. In particular, this may avoid an unintended break at a location which is not accessible, for example close to the reaming head. In other words, the predetermined breaking point or rated break point will be established in a safe and accessible region of the reaming device so that no broken parts of the reaming device remain in the patient's body.

According to an exemplary embodiment of the invention, the injection-molded interface element comprises a mold material having shape stability at common sterilization temperatures. Thus, it can be guaranteed that the reaming device cannot be sterilized without losing its particular geometry properties. This is of relevance if providing the reaming device as a single use device. In case, if the surgeon tries to use the reaming device again, he has to sterilize the reaming device, but during this sterilization, the reaming device will be predeterminently destroyed to avoid any reuse of the reaming device. It should be noted that either the entire interface element may be made of the non-heat resistant material, or only particular sections thereof may be made of the non-heat resistant material, if using for example a two stepped molding process using two different molding materials. It should also be noted that a heat resistant portion may be provided to maintain an "emergency" geometry, which however is not comfortable geometry for surgery. In particular one component of a multiple step mold may be heat resistant and the other component of a multiple step mold may be not heat resistant. The lost form stability may also be established by the impact of another parameter of sterilization, e.g. steam or the like. Thus, the interface element may be designed to lose its form stability when being treated by steam.

According to an exemplary embodiment of the invention, the injection-molded interface element comprises a deformation indicating pattern indicating a pre-breaking deformation. Thus, the surgeon can directly recognize a critical deformation of the interface element when recognizing the indicating pattern. This indicating pattern may be for example a longitudinal line or a longitudinal groove extending into the longitudinal direction of the interface element. In case the longitudinal groove or line deforms for example like a helix, the surgeon knows that a torque is applied, or that a particular threshold may be extended. It should be noted, that also an interfering grid may be used as a deformation indicating pattern, so that for example a particular Newton pattern may occur at particular stages of deformation, so that a particular Newton pattern may be used as an indicative for the grade of deformation.

According to an exemplary embodiment of the invention, both, the shaft and the interface element each have an elongated through bore, wherein the both through bores align to each other. Thus, a guide wire or a securing wire can be inserted into the aligning through bores. A guide wire may be used for an improved targeting of the reaming device, wherein a securing wire may be used for a reaming head being provided at the reaming device.

According to an exemplary embodiment of the invention, a method is provided for manufacturing a reaming device, comprising: wrapping a carbon fiber layer over an outer surface of a mounting portion of a shaft. A surface structure is pressed onto an outer surface of the carbon fiber layer. An interface layer is injection-molded over the surface structure. Thus, in particular when using a shaft made of a carbon fiber reinforced material, a carbon fiber layer may provide a reliable and compatible connection between the carbon fiber layer and the shaft. The outer surface structure of the carbon fiber layer establishes a reliable mechanical connection between the carbon fiber layer and the injection-molded interface element. In particular, such a method allows manufacturing a reaming device without having undue material tensions during a manufacturing process, as an injection-molding more or less provides a material morphology having a low or no material tensions.

According to an exemplary embodiment of the invention, wrapping comprises impregnating the carbon fiber layer with an impregnation agent being compatible with a material of the shaft. Thus, a reliable connection between the shaft and the carbon fiber layer may be established.

According to an exemplary embodiment of the invention, the method further comprises preparing a shaft mounting portion before wrapping a carbon fiber layer for establishing a reliable connection between the shaft and the carbon fiber layer. Thus, a kind of priming can be carried out before mounting the wrapped carbon fiber layer onto the shaft in order to establish a reliable connection being capable of transmitting torque.

According to an exemplary embodiment of the invention, pressing includes heat-setting of the carbon fiber layer in a closed mold. Thus, a fast and reliable manufacturing process can be established. In particular, when using a mold of a thermoplastic material and a thermosetting impregnation for the carbon fiber layer, a defined weak section can be established allowing a reliable transmission of forces and at the same time a predefined weak section as described above.

It should be noted that the above features may also be combined. The combination of the above features may also lead to a synergetic effect, even if not explicitly described herein in detail.

These and other aspects of the present invention will become apparent from and elucidated with reference to the embodiments described hereinafter.

BRIEF DESCRIPTION OF THE DRAWINGS

FIG. 1 illustrates a shaft for a reamer with a carbon fiber layer before wrapping;

FIG. 2 illustrates a shaft with a wrapped carbon fiber wrapping having a surface structure;

FIG. 3 illustrates a cross-sectional view of a shaft with an overmolded interface element;

FIG. 4 illustrates an outer view of a shaft with an overmolded interface element.

DETAILED DESCRIPTION

Figure 5:
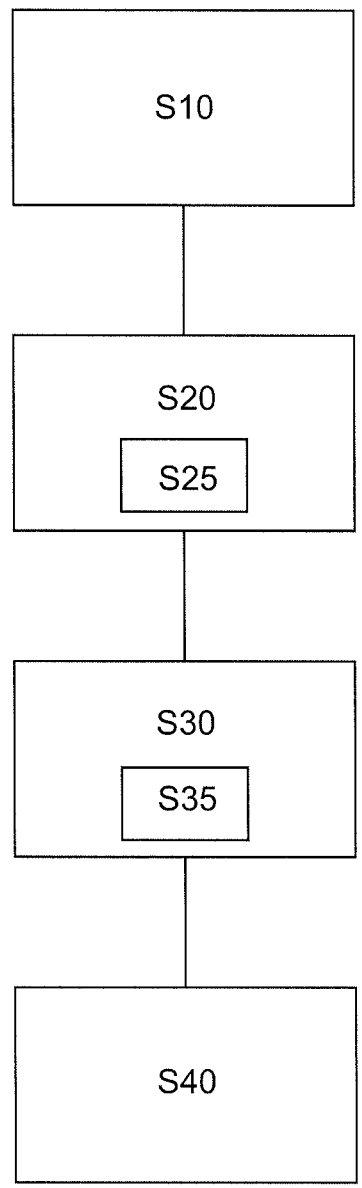
FIG. 5 illustrates a schematic flow chart of a method for manufacturing a reaming device.

FIG. 1 illustrates a shaft 10, in particular a reamer shaft having a mounting portion 11. The shaft 10 has an outer surface, onto which a carbon fiber layer 30 is wrapped. FIG. 1 illustrates the carbon fiber layer 30 in an unwrapped condition.

FIG. 2 illustrates the end portion of a shaft 10, wherein the carbon fiber layer 30 is wrapped around the outer surface of the mounting portion 11. As can be seen from FIG. 2, the carbon fiber layer comprises a surface structure 34 on the outer surface 33 of the carbon fiber layer. This outer structure may be formed for example as a tooth structure or a rippled or ripped structure, wherein ripples or rips run along a longitudinal direction of the shaft 10. It should be noted that the rips of the surface structure 34 may also run in a helical way in order to carry not only circumferential forces, e.g. torque forces, but also forces in a longitudinal direction of the shaft, like pushing or pulling forces. It should be noted that the surface structure 34 may also have any other structure being capable of transmitting forces from the shaft 10 to an interface element 20 or vice versa such as for example splines.

FIG. 3 illustrates a cross-sectional view of the end section of a shaft 10 provided with an overmolded interface element 20. The interface element 20 has a mounting portion 21, which engages with the surface structure of the carbon fiber layer outer surface 33, 34. Thus, forces can be transmitted from the shaft 10 to the interface element 20. The interface element and the shaft 10 both may comprise a through bore 19, 29, respectively, which through bores may align. Thus, a guide wire or a securing wire can be inserted through the aligned through bores 19, 29 so as to serve as a guide for the reaming tool and the reaming process, as well as securing for example a reaming head to be mounted on the other end section of the shaft (not shown). The injection-molded interface element 20 may comprise a rated break section 26, which may be for example a groove or a notch. As the interface element 20 also comprises a coupling portion 25, the rated break point section 26 can be provided between the mounting portion 21 on the one hand and the coupling portion 25 on the other hand. The coupling portion 25 may serve for coupling a power tool or a drive tool for driving the reaming device. By providing the rated weak section 26 between the coupling portion 25 and the mounting portion 21, an overburden of torque may lead to a predefined breakdown of the rated break section 26. As this section 26 may be designed as the weakest section with respect to a torque of the entire reaming device, a predefined breakdown or fracture of the rated section 26 avoids a breakdown or fracture on a more critical section, like for example close to the reamer head or the shaft being inserted into the patient's body. Thus, in case the reamer breaks, the rated break section provides a break location being outside of the body of the patient. The coupling portion 25 may further comprise a particular geometry for transmitting torque forces, for example the outer shape of a hexagonal cross-section in order to transmit torque forces. However, also a particular cross-sectional shape can be selected, which may be a unique cross-sectional shape which only fits to the corresponding power tool. Thus, it can be avoided that a not-matching combination of a reaming device and a power tool will be used.

The material of the injection-molded interface element may be a material which loses its outer shape when being exposed to a common sterilization or autoclave temperature (greater than about 120° C.). This may be of relevance when providing a reaming device for single use only. Thus, if trying to sterilize the reaming device, the outer shape of the interface element loses its predetermined shape, so that a further use of the reaming device is not possible. Thus, a re-use of a reaming device being intended for single use only can be avoided.

FIG. 4 illustrates the end portion of a reaming device having a shaft 10 and an injection-molded interface element 20. The injection-molded interface element 20 may be provided with a deformation indicating pattern 28. This deformation indicating pattern 28 may be for example a line extending into the longitudinal direction of the reaming device. In case, the interface element of the reaming device will deform, also the deformation indicating pattern will significantly deform, so that a surgeon will recognize the deformation. In particular, when stopping to apply a torque on the interface element, the shape of the deformation indicating pattern may be used as an indicative of a deformation of the interface element, even if no torque force is applied. If the interface element is deformed, it may be for example not used any longer. Such a deformation indicating pattern may be for example also an interference mesh or interference grid, so that depending on the deformation, several particular interference patterns may occur, which interference pattern may be used as an indicative for the strength of the deformation. This is illustrated as 28a and 28b. The pattern 28a is for example slightly inclined with respect to the longitudinal axis of the reaming device or the interface element 20, wherein the second pattern 28b has a counter inclination. When, for example, providing these both patterns 28a and 28b with an intermediate layer, so that the deformation for example will increase the inclination of the first pattern 28a, and decrease the inclination of the pattern 28b, an occurring interference pattern may be used as a unique indication for the extent of the deformation.

FIG. 5 illustrates a schematic flow of a method for manufacturing a reaming device. In step S10, the surface of the shaft may be prepared to provide an improved adhesion of the carbon fiber layer 30. This process may be considered as a kind of priming process. In step S20, the carbon fiber layer is wrapped over an outer surface of a mounting portion of a shaft. This wrapping optionally may comprise an impregnating process of the carbon fiber layer with an impregnation agent such as for example PEEK so as to increase the adhesion between the shaft 10 and the carbon fiber wrapping 30. In a subsequent step S30, a surface structure will be pressed on the outer surface of the carbon fiber layer. This can be carried out for example by a heated cast and the use of a thermosetting resin, so that step S30 may optionally include a heat setting process in step S35. Finally, an interface element 20 is injection-molded over the surface structure of the carbon fiber layer.

Example

The process for making a carbon fiber composite (CFC) reamer shaft will now be described:

A prepreg fabric (Sigratex CE 8011-200-42-SGL Group) is cut into specific pieces for the shaft and the connection area by using a cutter; for example an Aristomat TL 1617. The pieces are then wound on a metal core by using an automatic rolling table. Cellophane tape is then wound over the CFC shaft to fit it and to withstand the expansion during heating. This is done by using a shrink film wrapper. The CFC shaft is then hardened in an oven and the cellophane tape is removed. The CFC shaft is then ground to a tolerance of ±0.05 mm and the core is removed. A small piece of CFC prepreg is wound on the machine connection side to later get a form fit for the injection molding part. A metal dovetail and the drill side of the CFC shaft is threaded over a second core and a CFC prepreg fabric is wound over both ends to fix the dovetail and CFC shaft together. Any cavities present are filled with epoxy. The CFC shaft with dovetail and machine side is then fixed in a mold made of two semicirclar parts. By closing the mold the form fit for the later injection moulding of the machine connection and a homogenous smooth transition between dovetail and CFC shaft will be pressed on the shaft. The mold is heated in an oven again to harden the expoxy. Then the machine connection is insert molded with a torque limiter made of SLS on the CFC shaft.

It should be noted that the term "comprising" does not exclude other elements and that the term "a" or "an" does not exclude a plurality. Also elements described in association with the different embodiments may be combined.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for manufacturing a reaming device comprising:
    obtaining a carbon fiber composite shaft with an end mounting portion, the end mounting portion having an outer surface;
    wrapping a resin impregnated carbon fiber layer around the end mounting portion outer surface;
    pressing a tooth structure on an outer surface of the wrapped resin impregnated carbon fiber layer on the outer surface of the end mounting portion of the composite shaft; and
    injection molding completely over the pressed tooth structure of the wrapped carbon fiber layer an interface element made of a polymeric material which loses its outer shape at sterilization temperatures, the interface element having a connecting portion for mechanically connecting the shaft to a power tool, the interface element having an internal mounting portion for receiving the end mounting portion of the shaft with the wrapped carbon fiber layer, the interface element having a rated break section located between the drive tool connecting portion of the interface element and an end face of the internal mounting portion of the interface element receiving the end mounting portion of the shaft.

2. The method according to claim 1, wherein the shaft is made of a carbon fiber reinforced material.

3. The method according to claim 1, wherein the pressed tooth structure comprises an elongated rippled structure.

4. The method according to claim 1, wherein the injection molded interface element connecting portion is for coupling a power tool reamer drive as an external device.

5. The method according to claim 4, wherein the coupling portion comprises an end portion being capable of transmitting a torque.

6. The method according to claim 4, wherein the injection molded interface element rated break section is located between its mounting portion and its coupling portion.

7. The method according to claims 1, wherein both, the shaft and the injection molded interface element each have an elongated through bore, the both through bores aligning with each other.

8. The method of claim 1, wherein an outer surface of the interface element has a deformation pattern formed thereon indicating deformation thereof caused by torque applied to the shaft wherein the deformation pattern comprises first lines angled in a first direction with respect to a longitudinal axis of the shaft and second lines crossing the first lines at an opposite angle with respect to the longitudinal axis of the shaft.

9. A method for manufacturing a reaming device comprising:
    obtaining a drive shaft with a mounting portion, the mounting portion having an outer surface;
    forming a resin impregnated carbon fiber layer around the shaft mounting portion outer surface wherein the carbon fiber layer extends over the outer surface of the shaft mounting portion and pressing a tooth structure on an outer surface of the resin impregnated carbon fiber layer;
    thereafter forming an interface element on the carbon fiber layer on the shaft mounting portion by injection molding of a polymeric first portion of the interface element over the carbon fiber layer tooth structure and covering the same, the injection molded interface element having a connection portion configured for mechanical coupling to an external drive tool, and has an internal cavity for receiving the mounting portion of the drive shaft, the interface element having a rated break section located between the drive tool connection portion and an end face of the internal cavity for receiving the drive shaft mounting portion.

10. The method according to claim 9, wherein the shaft is made of a carbon fiber reinforced material.

11. The method according to claim 9, wherein the pressed tooth structure comprises an elongated rippled structure.

12. The method according to claim 9, wherein the injection molded interface element connecting portion is for coupling a power tool reamer drive as an external device.

13. The method according to claim 12, wherein the coupling portion comprises an end portion being capable of transmitting a torque.

14. The method according to claim 12, wherein the injection molded interface element rated break section is located between its mounting portion and its coupling portion.

15. The method according to claim 9, wherein the injection molded interface element comprises a mold material that loses shape stability at common sterilization temperatures.

16. The method of claim 9, wherein an outer surface of the interface element has a deformation pattern indicating deformation thereof caused by torque applied to the shaft wherein the deformation pattern comprises first lines angled in a first direction with respect to a longitudinal axis of the shaft and second lines crossing the first lines at an opposite angle with respect to the longitudinal axis of the shaft.

17. The method according to claims 9, wherein both, the shaft and the injection molded interface element each have an elongated through bore, the both through bores aligning with each other.

* * * * *